United States Patent [19]

Haga et al.

[11] 4,415,739

[45] Nov. 15, 1983

[54] PROCESS FOR PRODUCING 4-BENZOYLPYRAZOLES

[75] Inventors: Takahiro Haga, Kusatsu; Tetsuji Nishikawa, Moriyama; Toshio Nakajima, Kusatsu; Kohji Minamida, Shiga; Masaru Maeda, Hikone, all of Japan

[73] Assignee: Ishihara Sangyo Kaisha Ltd., Osaka, Japan

[21] Appl. No.: 400,025

[22] Filed: Jul. 20, 1982

[30] Foreign Application Priority Data

Aug. 3, 1981 [JP] Japan .................................. 56-121691
Jun. 11, 1982 [JP] Japan .................................. 57-100434

[51] Int. Cl.³ ............................................. C07D 23/20
[52] U.S. Cl. ..................................................... 548/367
[58] Field of Search .......................................... 548/367

[56] References Cited

U.S. PATENT DOCUMENTS 3,939,203  2/1976  Mattison et al. ..................... 564/266
4,070,536  1/1978  Kohotsune et al. ................. 548/367
4,146,726  3/1979  Kohotsune et al. ................. 548/367

OTHER PUBLICATIONS

Chem Abst. 1982, vol. 96, No. 85548q.

*Primary Examiner*—Henry R. Jiles
*Assistant Examiner*—Natalia Harkaway
*Attorney, Agent, or Firm*—Oblon, Fisher, Spivak, McClelland & Maier

[57] ABSTRACT

4-Benzoyl-5-hydroxypyrazoles useful as herbicidal active ingredients, their intermediate or stabilizers against heat, oxidation or ultraviolet light are produced by a condensation of a pyrazolone, tetrachloromethane and a benzene compound in the presence of an aluminium halide, followed by a hydrolysis reaction with industrial advantages.

10 Claims, No Drawings

PROCESS FOR PRODUCING 4-BENZOYLPYRAZOLES

BACKGROUND OF THE INVENTION

1. Field of the Invention

The present invention relates to a process for producing 4-benzoyl-5-hydroxypyrazoles or basic salts formed by the hydroxy group thereof (hereinafter referring to as 4-benzoylpyrazole derivatives) which are useful as active ingredients or intermediates of herbicides, or stabilizers against heat, oxidation or ultraviolet light. More particularly, it relates to a process for producing 4-benzoylpyrazole derivatives by a condensation reaction of a pyrazolone derivative, tetrachloromethane and a benzene derivative in the presence of an aluminium halide followed by a hydrolysis reaction.

2. Description of the Prior Arts

Heretofore, it has been known to produce 4-benzoylpyrazole derivatives by a reaction of a pyrazolone derivative with a benzoyl halide derivative in U.S. Pat. No. 4,063,925; and U.S. Pat. No. 4,008,200. In the processes, a 5-benzoyloxypyrazole derivative is produced as an intermediate and then, the benzoyl group at 5-position of the intermediate is rearranged at 4-position to obtain a 4-benzoylpyrazole derivative. Thus, the benzoyl halide derivatives used as the starting materials in the process have irritative properties and they are difficult to handle. Moreover, the benzoyl halide derivative has been produced by a chlorination reaction of a side chain of toluene or a halogenotoluene followed by a hydrolysis reaction of the resulting product. The benzoyl halide derivative has been also produced by oxidizing toluene or halogenotoluene and reacting the resulting benzoic acid derivative with phosphorus trichloride, phosgen or thionyl chloride. The process comprises many steps and is expensive.

Further, the present inventors have filed a patent application in the United States (U.S. patent application Ser. No. 240,313) which relates to a process for producing a 4-benzoylpyrazole derivatives by a condensation reaction of a pyrazolone derivative and a benzotrichloride derivative, followed by a hydrolysis reaction. However, the process still has certain industrial disadvantages.

SUMMARY OF THE INVENTION

It is an object of the present invention to provide a process for producing 4-benzoylpyrazole derivatives.

It is another object of the present invention to provide a process for producing 4-benzoylpyrazole derivatives with industrial advantages by using economical starting materials in simple operations.

The other objects of the present invention will be apparent by the following description.

In accordance with the present invention, it provides a process for producing a 4-benzoyl-5-hydroxypyrazole represented by the formula I;

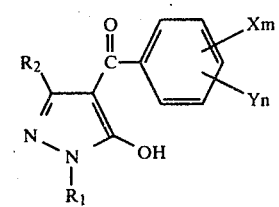

wherein $R_1$ is a hydrogen atom or an alkyl group, $R_2$ is an alkyl group, X is a halogen atom, Y is an alkyl group, m is an integer of 1 to 5, n is an integer of 0 to 2 with the proviso that m is not less than n, or basic salts formed by the hydroxy group of the pyrazoles which comprises a condensation reaction of a pyrazolone represented by the formula II;

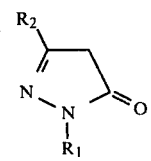

wherein $R_1$ and $R_2$ are as defined above, tetrachloromethane and a benzene compound represented by the formula III;

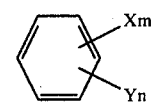

wherein X, Y, m and n are as defined above, in the presence of an aluminium halide at a temperature of 0° C. to 100° C., followed by a hydrolysis reaction at a temperature of 0° C. to 150° C.

DETAILED DESCRIPTION OF THE PREFERRED EMBODIMENTS

It has been found that 4-benzoylpyrazole derivatives as the object compounds are produced by directly condensing a pyrazolone derivative, tetrachloromethane and a benzene compound in the presence of an aluminium halide, and then hydrolyzing the condensation product. The aluminium halide used in the present invention can be an anhydrous aluminium chloride or an aluminium bromide, etc.

In the formulas I, II and III, the alkyl group as $R_1$, $R_2$ and Y can be a methyl, ethyl, isopropyl or tert-butyl group, etc.; the halogen atom as X can be a fluorine, chlorine, bromine or iodine atom, etc.; and the substituents as $X_m$ and $Y_n$ with m and n being 2 or more than 2 can be same or different.

The pyrazolone derivatives represented by the formula II can be exemplified as follows: 3-methyl-5-pyrazolone, 1,3-dimethyl-5-pyrazolone, 3-ethyl-5-pyrazolone, 3-methyl-1-(isopropyl)-5-pyrazolone, etc., and the benzene compounds represented by the formula (III) can be exemplified as follows: chlorobenzene, bromobenzene, o-, m- or p-dichlorobenzene, 1,2,4- or 1,3,5-trichlorobenzene, 2,4-dichlorotoluene, 2,6-dichlorotoluene, 2,3,6-trichlorotoluene, 2,5-dichlorotoluene, 2,4,6-trichlorotoluene, 2,4-dichloroethylbenzene, 2,6-dichloroethylbenzene, 4,5-dichloro-o-xylene, 2,4-dichloro-m-xylene, ektc.

In accordance with the process of the present invention, economical starting materials can be used and 4-benzoylpyrazole derivatives as the object products can be easily produced in high yield, for example, higher than 90% with industrial advantages in comparison with the conventional processes.

In accordance with the process of the present invention, the condensation reaction of the pyrazolone derivative, the tetrachloromethane and the benzene compound in the presence of an aluminium halide is usually carried out at a temperature ranging from 0° C. to 100° C., preferably 10° C. to 70° C., and then, the hydrolysis reaction of the condensation product is carried out.

The condensation reaction mixture can be hydrolyzed by subjecting it to usual hydrolysis reaction after discharging it from the reaction system. However, it is usually preferable to hydrolyze it by adding water containing acid to it without discharging it from the reaction system.

The amounts of the starting materials and aluminium halide used in the present invention are not critical and depend upon the substances, reaction conditions and the like in the condensation reaction. It is preferable that they are used in an equimole or a somewhat excess of the equimole like in usual condensation reactions. It is undesirable that they cause a decrease in the yield of the objective product when they are considerably less than the equimole, and they increase the formation of a by-product when they are considerably in excess of the equimole. In general, the amounts of the benzene compound and the tetrachloromethane are in ranges of 1 to 3 mole and 1 to 5 mole per 1 mole of the pyrazolone derivative, respectively. Further the amount of aluminum halide is 2 to 3 mole per 1 mole of the pyrazolone derivative.

The condensation reaction does not necessarily need a presence of a solvent. However, it is preferable that the condensation reaction is carried out in the presence of a solvent. Any solvent can be used so long as it does not adversely affect the condensation reaction. The solvent can be a halogenated hydrocarbon such as methylene chloride, dichloroethane and tetrachloroethane, trichlorobenzene, etc. or carbon disulfide. The condensation reaction is performed industrially by selecting appropriate conditions from the above-mentioned ones. It is preferable that the condensation reaction is performed after anhydrous aluminum chloride is added to a solution which contains the pyrazolone derivative and the solvent, if necessary together with one or two kinds of the remained starting materials of the present invention.

The hydrolysis reaction in the process of the present invention is usually carried out by adding water to the reaction product obtained by the condensation reaction. For example, after confirming the completion of the condensation reaction, the hydrolysis reaction of the reaction product is uaually carried out without discharging the reaction mixture at a temperature ranging from 0° C. to 150° C. preferably room temperature to 100° C., especially from 40° C. to 80° C., by adding an aqueous solution of a mineral acid such as hydrochloric acid and sulfuric acid etc. in a molar ratio of 3 to 10, preferably 4 to 6, based thereon. The hydrolysis reaction may be carried out after the solvent is distilled off from the reaction product. It is industrially preferable that the reaction mixture is discharged from the reaction product and washed by water, and then the mineral acid is added to it to perform the hydrolysis reaction.

Reaction times for the condensation reaction and the hydrolysis reaction of the present invention are not critical and selected depending upon the other conditions of the reactions and are respectively usually in a range of 0.2 to 10 hours. After the completion of the reaction, the reaction mixture is treated by the conventional separation and purification such as a solvent extraction, an alkali treatment, and an acid treatment to obtain 4-benzoylpyrazole derivative as the object product.

The present invention will be further illustrated by certain examples and references which are provided for purposes of illustration only and are not intended to be limiting the present invention.

EXAMPLE 1

To a mixed solution of 5.6 g of 1,3-dimethyl-5-pyrazolone and 40 ml of dichloroethane was added 20 g of anhydrous aluminium chloride while cooling the solution by water. Then a solution of 8.8 g of m-dichlorobenzene, 15.4 g of tetrachloromethane and 20 ml of dichloroethane was dropwise added to the mixed solution at 45° to 50° C. in one hour and a condensation reaction was performed at the same temperature for 30 minutes. The reaction mixture was poured into 250 ml of ice water, washed with water, and subjected to a liquid phase separation to obtain a dichloroethane solution.

To the dichloroethane solution were dropwise added 4 ml of sulfuric acid and 2 ml of water at 60° to 65° C. and a hydrolysis reaction was performed at the same temperature for 2 hours. The reaction product was poured into water, washed with water, extracted with an aqueous solution of a saturated sodium bicarbonate, treated with hydrochloric acid, extracted with methylenechloride, and dried over sodium sulfate and the solvent was distilled off to obtain 10.4 g of 1,3-dimethyl-4-(2,4-dichlorobenzoyl)-5-hydroxypyrazole.

EXAMPLE 2

To a mixed solution of 5.6 g of 1,3-dimethyl-5-pyrazolone and 40 ml of dichloroethane was added 16 g of anhydrous aluminium chloride while cooling the solution by water, and 9.6 g of m-dichlorobenzene was dropwise added thereto at 30° C. Then a solution of 15.4 g of tetrachloromethane and 20 ml of dichloroethane was dropwise added to the mixed solution at 25° to 30° C. in one hour and a condensation reaction was performed at 40° C. for 90 minutes and at 50° C. for 30 minutes. The reaction mixture was allowed to cool and 100 ml of concentrated hydrochloric acid was gradually added to it and a reaction was performed at 60° to 70° C. for 4 hours. The dichloroethane solution was separated partially and refined in the same manner as in Example 1 to obtain 13.2 g of 1,3-dimethyl-4-(2,4-dichlorobenzoyl)-5-hydroxypyrazole.

EXAMPLE 3

In accordance with the process of Example 2 except for changing 40 ml and 20 ml of dichloroethane as a solvent dissolving raw materials to 40 ml and 20 ml, respectively, of carbon disulfide, and 16 g of anhydrous aluminum chloride to 16.7 g of one, the condensation reaction and post-treatment were carried out. Then, in accordance with the process of Example 1, the hydrolysis reaction and refinement were carried out to obtain 5.2 g of 1,3-dimethyl-4-(2,4-dichlorobenzoyl)-5-hydroxypyrazole.

EXAMPLE 4

In accordance with the process of Example 2 except for changing 40 ml and 20 ml of dichloroethane as a solvent dissolving raw materials to 40 ml and 20 ml, respectively, of methylene chloride, and 16 g of anhydrous aluminum chloride to 16.7 g of one, the condensation reaction and post-treatment were carried out. Then, in accordance with the process of Example 1, the hydrolysis reaction and refinement were carried out to obtain 9.7 g of 1,3-dimethyl-4-(2,4-dichlorobenzoyl)-5-hydroxypyrazole.

EXAMPLE 5

To a mixed solution of 4.9 g of 3-methyl-5-pyrazolone and 40 ml of dichloroethane was added 16.7 g of anhydrous aluminum chloride while cooling the solution by water and 9.6 g of m-dichlorobenzene was dropwise added thereto at 30° C. Then, a solution of 11.6 g of tetrachloromethane and 20 ml of dichloroethane was dropwise added to the mixed solution at 25° to 30° C. in one hour and a condensation reaction was performed at 30° C. for 90 minutes and at 50° C. for 30 minutes. The reaction mixture was poured into 250 ml of ice water, washed with water and subjected to a liquid phase separation to obtain a dichloroethane solution. Then, in accordance with the process of Example 1 the hydrolysis reaction and refinement were carried out to obtain 13.2 g of 3-methyl-4-(2,4-dichlorobenzoyl)-5-hydroxypyrazole.

EXAMPLE 6

To a mixed solution of 5.6 g of 1,3-dimethyl-5-pyrazolone, 60 ml of tetrachloromethane and 9.6 g of m-dichlorobenzene was added 16.7 g of anhydrous aluminum chloride at 20° C. in one hour, and a condensation reaction was performed at 30° C. for 2 hours, at 40° C. for one hour and at 50° C. for 30 minutes. The reaction mixture was poured into 300 ml of ice water, washed with water and subjected to a liquid phase separation to obtain a tetrachloromethane solution.

Then, in accordance with the process of Example 1, the hydrolysis reaction and refinement were carried out to obtain 4.3 g of 1,3-dimethyl-4-(2,4-dichlorobenzoyl)-5-hydroxypyrazole.

EXAMPLE 7

To a mixed solution of 5.6 g of 1,3-dimethyl-5-pyrazolone, 60 ml of dichloroethane, 9.6 g of m-dichlorobenzene and 11.6 g of tetrachloromethane was added 16.7 g of anhydrous aluminum chloride at 20° C. in one hour, and a condensation reaction was performed at 30° C. for 2 hours, at 40° C. for one hour and at 50° C. for 30 minutes. The reaction mixture was poured into 300 ml of ice water, washed with water and subjected to a liquid phase separation to obtain a dichloroethane solution.

Then, in accordance with the process of Example 1, the hydrolysis reaction and refinement were carried out to obtain 13.3 g of 1,3-dimethyl-4-(2,4-dichlorobenzoyl)-5-hydroxypyrazole.

EXAMPLE 8

To a mixed solution of 5.6 g of 1,3-dimethyl-5-pyrazolone and 40 ml of dichloroethane was added 16.7 g of anhydrous aluminum chloride while cooling the solution by water and 7.3 g of chlorobenzene was dropwise added thereto at 30° C. Then, a solution of 11.6 g of tetrachloromethane and 20 ml of dichloroethane was dropwise added to the mixed solution at 25° to 30° C. in one hour and a condensation reaction was performed at the same temperature for one hour, at 40° C. for one hour and at 50° C. for 30 minutes. The reaction mixture was poured into 300 ml of ice water, washed with water and subjected to a liquid phase separation to obtain a dichloroethane solution. Then, in accordance with the process of Example 1, the hydrolysis reaction and refinement were carried out to obtain 5.6 g of 1,3-dimethyl-4-(4-chlorobenzoyl)-5-hydroxypyrazole.

Further, in accordance with the process of Example 8 except for changing chlorobenzene to bromobenzene or 1,3,5-trichlorobenzene, the condensation reaction, hydrolysis reaction, refinement and the like were carried out to obtain respectively 1,3-dimethyl-4-(4-bromobenzoyl)-5-hydroxypyrazole or 1,3-dimethyl-4-(2,4,6-trichlorobenzoyl)-5-hydroxypyrazole.

EXAMPLE 9

To a mixed solution of 5.6 g of 1,3-dimethyl-5-pyrazolone and 40 ml of dichloroethane was added 16.7 g of anhydrous aluminum chloride while cooling the solution by water and a solution of 10.5 g of 2,6-dichlorotoluene, 10 g of tetrachloromethane and 20 ml of dichloroethane was added to the mixed solution at 30° to 35° C. in 30 minutes and a condensation reaction was performed at the same temperature for 4 hours. The reaction mixture was poured into 250 ml of ice water, washed with water and subjected to a liquid phase separation to obtain a dichloroethane solution.

To the dichloroethane solution were dropwise added 4 ml of sulfuric acid and 2 ml of water at 60° to 65° C. and a hydrolysis reaction was performed at the same temperature for 2 hours. The reaction product was poured into water, washed with water, extracted with a 5% aqueous solution of sodium hydroxide, treated with hydrochloric acid, extracted with methylene chloride, and dried over sodium sulfate and the solvent was distilled off to obtain 13.8 g of 1,3-dimethyl-4-(2,4-dichloro-3-methylbenzoyl)-5-hydroxypyrazole.

EXAMPLE 10

In accordance with the process of Example 9 except for changing 40 ml and 20 ml of dichloroethane as a solvent dissolving raw materials to 40 ml and 20 ml, respectively, of 1,1,2-trichloroethane, the condensation reaction and post-treatment were carried out. Then, in accordance with the process of Example 9, the hydrolysis reaction and refinement were carried out to obtain 11.1 g of 1,3-dimethyl-4-(2,4-dichloro-3-methylbenzoyl)-5-hydroxypyrazole.

EXAMPLE 11

To a mixed solution of 4.9 g of 3-methyl-5-pyrazolone and 40 ml of dichloroethane was added 16.7 g of anhydrous aluminum chloride while cooling the solution by water and 10.5 g of 2,6-dichlorotoluene was dropwise added thereto at 30° C. A solution of 10 g of tetrachloromethane and 20 ml of dichloroethane was dropwise added to the mixed solution at 25° to 30° C. in one hour and a condensation reaction was performed at 30° C. for 90 minutes and at 50° C. for 30 minutes. The reaction mixture was poured into 250 ml of ice water, washed with water and subjected to a liquid phase separation to obtain a dichloroethane solution. Then, in accordance with the process of Example 9, the hydrolysis reaction and refinement were carried out to obtain 13.2 g of 3-methyl-4-(2,4-dichloro-3-methylbenzoyl)-5-hydroxypyrazole.

EXAMPLE 12

To a mixed solution of 5.6 g of 1,3-dimethyl-5-pyrazolone, 60 ml of dichloroethane, 10.5 g of 2,4-dichlorotoluene and 10 g of tetrachloromethane was added 16.7 g of anhydrous aluminum chloride at 20° C. in one hour and a condensation reaction was performed at 30° C. for 2 hours and at 40° C. for one hour. The reaction mixture was poured into 300 ml of ice water, washed with water and subjected to a liquid phase separation to obtain a dichloroethane solution.

Then, in accordance with the process of Example 9, the hydrolysis reaction and refinement were carried out to obtain 14.3 g of 1,3-dimethyl-4-(2,4-dichloro-5-methylbenzoyl)-5-hydroxypyrazole.

EXAMPLE 13

In accordance with the process of Example 9 except for adding dropwise a solution of 12.7 g of 2,3,6-trichlorotoluene at 40° C. in 30 minutes and performing a condensation reaction at the same temperature for 2 hours, the condensation reaction, hydrolysis reaction and refinement were carried out to obtain 14.7 g of mixture of 1,3-dimethyl-4-(2,3,5-trichloro-4-methylbenzolyl)-5-hydroxypyrazole and 1,3-dimethyl-4-(2,4,5-trichloro-3-methylbenzoyl)-5-hydroxypyrazole.

We claim:

1. A process for producing a 4-benzoyl-5-hydroxypyrazole represented by the formula (I):

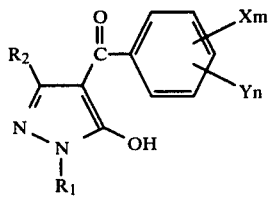

wherein $R_1$ is a hydrogen atom or an alkyl group, $R_2$ is an alkyl group, X is a halogen atom, Y is an alkyl group, m is an integer of 1 to 5, n is an integer of 0 to 2 with the proviso that m is not less than n, or basic salts formed by the hydroxy group of the pyrazoles which comprises a condensation reaction of a pyrazolone represented by the formula II:

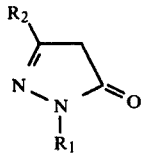

wherein $R_1$ and $R_2$ are as defined above, tetrachloromethane and a benzene compound represented by the formula III:

wherein X, Y, m and n are as defined above, in the presence of an aluminum halide at a temperature of 0° C. to 100° C., followed by a hydrolysis reaction at a temperature of 0° C. to 150° C.

2. The process according to claim 1 wherein said pyrazolone is represented by the formula

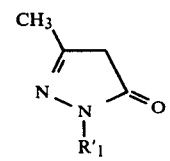

wherein $R'_1$ is a hydrogen atom or a methyl group, said benzene compound is represented by the formula

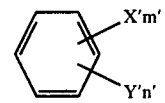

wherein X' is a chlorine atom, Y' is a methyl group, m' is an integer of 1 to 3 and n' is 0 or 1 and said 4-benzoyl-5-hydroxypyrazole is represented by the formula

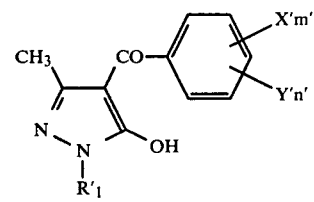

wherein $R'_1$, X', Y', m' and n' are as defined above.

3. The process according to claim 1 wherein said pyrazolone is 1,3-dimethyl-5-pyrazolone, said benzene compound is m-dichlorobenzene or 2,6-dichlorotoluene and said 4-benzoyl-5-hydroxypyrazole is 1,3-dimethyl-4-(2,4-dichlorobenzoyl)-5-hydroxypyrazole or 1,3-dimethyl-4-(2,4-dichloro-3-methylbenzoyl)-5-hydroxypyrazole.

4. The process according to claim 1 wherein said pyrazolone is 1,3-dimethyl-5-pyrazolone, said benzene compound is m-dichlorobenzene and said 4-benzoyl-5-hydroxypyrazole is 1,3-dimethyl-4-(2,4-dichlorobenzoyl)-5-hydroxypyrazole.

5. The process according to claim 1 wherein the condensation reaction is carried out in the presence of aluminum chloride.

6. The process according to claim 1 wherein the condensation reaction is carried out in the presence of a solvent selected from a halogenated hydrocarbon or carbon disulfide.

7. The process according to claim 1 wherein the condensation reaction is carried out in the presence of dichloroethane as solvent.

8. The process according to claim 1 wherein the condensation reaction is carried out at a temperature of 10° C. to 70° C.

9. The process according to claim 1 wherein the hydrolysis reaction is carried out by using an aqueous solution containing a mineral acid.

10. The process according to claim 1 wherein the hydrolysis reaction is carried out at a temperature of room temperature to 100° C.

* * * * *